United States Patent
Eriksen et al.

(10) Patent No.: US 8,222,262 B2
(45) Date of Patent: Jul. 17, 2012

(54) INDAZOLYL DERIVATIVES USEFUL AS POTASSIUM CHANNEL MODULATING AGENTS

(75) Inventors: Birgitte L. Eriksen, Farum (DK); Ulrik Svane Sørensen, Søborg (DK); Charlotte Hougaard, Bagsværd (DK); Lene Teuber, Værløse (DK); Dan Peters, Malmö (SE); Palle Christophersen, Ballerup (DK); Tina Holm Johansen, Smørum (DK)

(73) Assignee: Neurosearch A/S, Ballerup (DK)

( * ) Notice: Subject to any disclaimer, the term of this patent is extended or adjusted under 35 U.S.C. 154(b) by 147 days.

(21) Appl. No.: 12/444,344

(22) PCT Filed: Oct. 3, 2007

(86) PCT No.: PCT/EP2007/060493
§ 371 (c)(1), (2), (4) Date: Jul. 1, 2009

(87) PCT Pub. No.: WO2008/040753
PCT Pub. Date: Apr. 10, 2008

(65) Prior Publication Data
US 2009/0325989 A1   Dec. 31, 2009

Related U.S. Application Data

(60) Provisional application No. 60/827,940, filed on Oct. 3, 2006.

(30) Foreign Application Priority Data

Oct. 3, 2006  (DK) ................................. 2006 01280

(51) Int. Cl.
*A61K 31/517* (2006.01)

(52) U.S. Cl. ............... 514/266.2; 544/284; 544/287; 544/293; 544/333

(58) Field of Classification Search ............. 544/284, 544/287, 293, 333
See application file for complete search history.

(56) References Cited

U.S. PATENT DOCUMENTS

2004/0116429 A1 * 6/2004 Grote et al. ................. 514/242

FOREIGN PATENT DOCUMENTS

| WO | WO-2004/078733 A1 | 9/2004 |
|---|---|---|
| WO | WO-2005/054230 A1 | 6/2005 |
| WO | WO-2006/097441 A1 | 9/2006 |
| WO | WO-2006/100212 A1 | 9/2006 |
| WO | WO-2007/042571 A1 | 4/2007 |
| WO | WO-2007/071632 A2 | 6/2007 |

OTHER PUBLICATIONS

Database Registry CAS: 501918-48-5, Apr. 7, 2003, XP-002466289-abstract only.

* cited by examiner

*Primary Examiner* — James O Wilson
*Assistant Examiner* — Brian McDowell
(74) *Attorney, Agent, or Firm* — Birch, Stewart, Kolasch & Birch, LLP

(57) ABSTRACT

Potassium channel modulating agents of Formula Ia or Ib

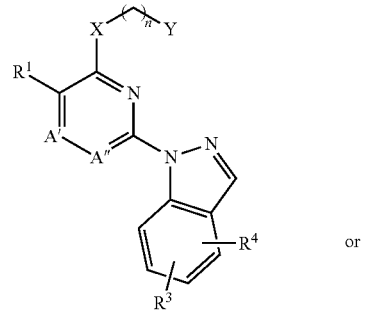

(Ia)

or

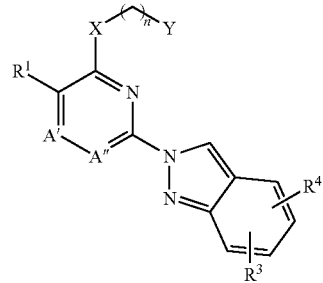

(Ib)

and enantiomers and mixtures enantiomers and N-oxides thereof, and pharmaceutically acceptable salts thereof, and their use in the preparation of pharmaceutical compositions. Also, pharmaceutical compositions useful for the treatment or alleviation of diseases or disorders associated with the activity of potassium channels, e.g., respiratory diseases, epilepsy, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, schizophrenia, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labor, baldness, cancer, immune suppression, or pain.

20 Claims, No Drawings

INDAZOLYL DERIVATIVES USEFUL AS POTASSIUM CHANNEL MODULATING AGENTS

This application is the National Phase of PCT/EP2007/060493 filed on Oct. 3, 2007, which claims priority under 35 U.S.C. 119(e) to U.S. Provisional Application No. 60/827,940 filed on Oct. 3, 2006, and under 35 U.S.C. 119(a) to Patent Application No. PA 2006 01280 filed in Denmark on Oct. 3, 2006, all of which are hereby expressly incorporated by reference into the present application.

TECHNICAL FIELD

This invention relates to novel indazolyl derivatives useful as potassium channel modulating agents, and their use in the preparation of pharmaceutical compositions.

Moreover the invention is directed to pharmaceutical compositions useful for the treatment or alleviation of diseases or disorders associated with the activity of potassium channels, in particular respiratory diseases, epilepsy, convulsions, seizures, absence seizures, vascular spasms, coronary artery spasms, renal disorders, polycystic kidney disease, bladder spasms, urinary incontinence, bladder outflow obstruction, erectile dysfunction, gastrointestinal dysfunction, secretory diarrhoea, ischaemia, cerebral ischaemia, ischaemic heart disease, angina pectoris, coronary heart disease, autism, ataxia, traumatic brain injury, Parkinson's disease, bipolar disorder, psychosis, schizophrenia, anxiety, depression, mania, mood disorders, dementia, memory and attention deficits, Alzheimer's disease, amyotrophic lateral sclerosis (ALS), dysmenorrhea, narcolepsy, Reynaud's disease, intermittent claudication, Sjorgren's syndrome, arrhythmia, hypertension, myotonic muscle dystrophia, spasticity, xerostomi, diabetes type II, hyperinsulinemia, premature labour, baldness, cancer, irritable bowel syndrome, immune suppression, migraine and pain.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

SK channels are present in many central neurons and ganglia, where their primary function is to hyperpolarize nerve cells following one or several action potentials, in order to prevent long trains of epileptogenic activity to occur. The SK channels are also present in several peripheral cells including skeletal muscle, gland cells, liver cells, and T-lymphocytes.

The significance of SK channels in normal skeletal muscle is not clear, but their number is significantly increased in denervated muscle, and the large number of SK channels in the muscle of patients with myotonic muscle dystrophia, suggest a role in the pathogenesis of the disease.

Studies indicate that $K^+$ channels may be a therapeutic target in the treatment of a number of diseases including asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer and immune suppression.

SUMMARY OF THE INVENTION

The present invention resides in the provision of novel indazolyl derivatives capable of selectively modulating SK channels, or subtypes of SK channels.

Moreover the invention is directed to pharmaceutical compositions useful for the treatment or alleviation of diseases or disorders associated with the activity of potassium channels, including diseases or conditions like respiratory disease, epilepsy, convulsions, seizures, absence seizures, vascular spasms, coronary artery spasms, renal disorders, polycystic kidney disease, bladder spasms, urinary incontinence, bladder outflow obstruction, erectile dysfunction, gastrointestinal dysfunction, secretory diarrhoea, ischaemia, cerebral ischaemia, ischaemic heart disease, angina pectoris, coronary heart disease, autism, ataxia, traumatic brain injury, Parkinson's disease, bipolar disorder, psychosis, schizophrenia, anxiety, depression, mania, mood disorders, dementia, memory and attention deficits, Alzheimer's disease, amyotrophic lateral sclerosis (ALS), dysmenorrhea, narcolepsy, Reynaud's disease, intermittent claudication, Sjorgren's syndrome, arrhythmia, hypertension, myotonic muscle dystrophia, spasticity, xerostomi, diabetes type II, hyperinsulinemia, premature labour, baldness, cancer, irritable bowel syndrome, immune suppression, migraine or pain.

Accordingly, in its first aspect, the invention provides novel indazolyl derivatives of Formula Ia or Ib

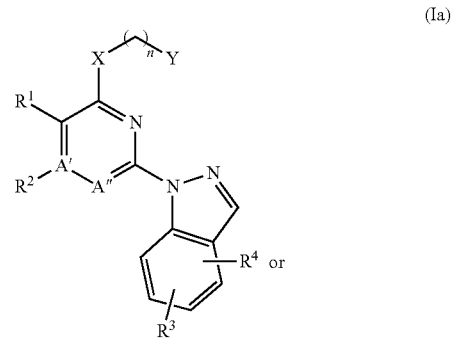

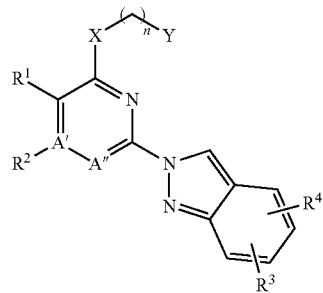
(Ib)

an enantiomer or a mixture of its enantiomers, an N-oxide thereof, or a pharmaceutically acceptable salt thereof, wherein n is 0, 1, 2 or 3;

X represents O, S or NR'; wherein R' represents hydrogen, alkyl, cycloalkyl or cycloalkyl-alkyl;

Y represents alkyl, alkyl-cycloalkyl, cycloalkyl, cycloalkyl-alkyl, amino-alkyl, alkyl-amino, alkyl-amino-alkyl, hydroxy-alkyl, alkoxy-alkyl, alkenyl, or phenyl, which phenyl may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro and amino;

A' represents N or $CR^2$, wherein $R^2$ is as defined below; and

A" represents N or CH;

provided, however, that only one of A' and A" represents N; and $R^1$, $R^2$, $R^3$ and $R^4$ independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; or $R^1$ and $R^2$ together with the heteroaromatic ring to which they are attached form a benzo-fused ring; and $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In another aspect, the invention provides pharmaceutical compositions comprising an effective amount of the indazolyl derivatives of the invention.

Viewed from another aspect the invention relates to the use of an indazolyl derivative of the invention for the manufacture of a medicament for the treatment or alleviation of diseases or disorders associated with the activity of potassium channels, and to method of treatment or alleviation of disorders or conditions responsive to modulation of potassium channels.

In a further aspect the invention provides methods of treatment, prevention or alleviation of a disease or a disorder or a condition of a living animal body, including a human, which disease, disorder or condition is responsive to modulation of the potassium channels, and which method comprises comprising administering to such a living animal body, including a human, in need thereof a therapeutically-effective amount of an indazolyl derivative of the invention.

DETAILED DISCLOSURE OF THE INVENTION

Potassium Channel Modulating Agents

In its first aspect the invention provides novel 1- or 2-indazolyl derivatives of Formula Ia or Ib

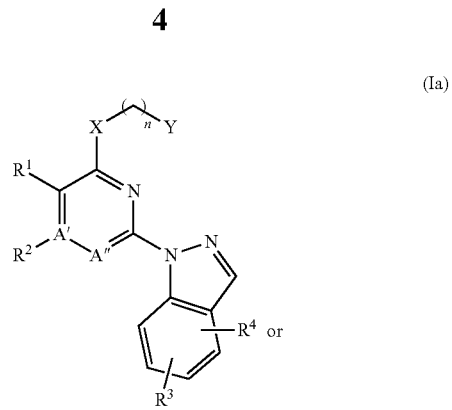

an enantiomer or a mixture of its enantiomers, an N-oxide thereof, or a pharmaceutically acceptable salt thereof, wherein n is 0, 1, 2 or 3;

X represents O, S or NR'; wherein R' represents hydrogen, alkyl, cycloalkyl or cycloalkyl-alkyl;

Y represents alkyl, alkyl-cycloalkyl, cycloalkyl, cycloalkyl-alkyl, amino-alkyl, alkyl-amino, alkyl-amino-alkyl, hydroxy-alkyl, alkoxy-alkyl, alkenyl, or phenyl, which phenyl may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro and amino;

A' represents N or $CR^2$, wherein $R^2$ is as defined below; and

A" represents N or CH;

provided, however, that only one of A' and A" represents N; and $R^1$, $R^2$, $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; or $R^1$ and $R^2$ together with the heteroaromatic ring to which they are attached form a benzo-fused ring; and $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In a preferred embodiment the indazolyl derivative of the invention is a 1-indazolyl derivative of Formula Ia, or a 2-indazolyl derivative of Formula Ib.

In a more preferred embodiment the indazolyl derivative of the invention is a 1-indazolyl derivative of Formula Ia.

In another more preferred embodiment the indazolyl derivative of the invention is a 2-indazolyl derivative of Formula Ib.

In another preferred embodiment the indazolyl derivative of the invention is an indazolyl derivative of Formula Ia or Ib, wherein n is 0, 1, 2 or 3.

In a more preferred embodiment n is 0, 1 or 2.

In an even more preferred embodiment n is 0 or 1.

In a still more preferred embodiment n is 0.

In another still more preferred embodiment n is 1.

In a third preferred embodiment the indazolyl derivative of the invention is an indazolyl derivative of Formula Ia or Ib, wherein X represents O, S or NR'; wherein R' represents hydrogen, alkyl, cycloalkyl or cycloalkyl-alkyl.

In a more preferred embodiment X represents NR'; wherein R' represents hydrogen or alkyl.

In an even more preferred embodiment X represents NH.

In a fourth preferred embodiment the indazolyl derivative of the invention is an indazolyl derivative of Formula Ia or Ib, wherein Y represents alkyl, alkyl-cycloalkyl, cycloalkyl, cycloalkyl-alkyl, amino-alkyl, alkyl-amino, alkyl-amino-alkyl, hydroxy-alkyl, alkoxy-alkyl, alkenyl, or phenyl, which phenyl may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro and amino.

In a more preferred embodiment Y represents alkyl, alkyl-cycloalkyl, cycloalkyl or phenyl, which phenyl may optionally be substituted one or more times with substituents selected from the group consisting of alkyl, cycloalkyl, halo, haloalkyl, haloalkoxy, cyano, nitro and amino.

In an even more preferred embodiment Y represents alkyl-cycloalkyl, cycloalkyl or phenyl, which phenyl may optionally be substituted one or more times with substituents selected from the group consisting of halo, in particular fluoro, chloro, bromo, or iodo, trifluoromethyl, trifluoromethoxy, cyano, nitro and amino.

In a still more preferred embodiment Y represents cycloalkyl, in particular cyclopentyl, cyclohexyl, or cycloheptyl, or phenyl, which phenyl may optionally be substituted one or more times with substituents selected from the group consisting of halo, in particular fluoro, chloro, bromo or iodo, trifluoromethyl and trifluoromethoxy.

In a yet more preferred embodiment Y represents cycloalkyl, in particular cyclopentyl, cyclohexyl, or cycloheptyl.

In a most preferred embodiment Y represents cyclohexyl.

In a further more preferred embodiment Y represents phenyl, which phenyl may optionally be substituted with halo, in particular fluoro, chloro, bromo or iodo, or trifluoromethyl.

In a further more preferred embodiment Y represents phenyl, optionally substituted with halo, in particular fluoro, chloro, bromo or iodo.

In a fifth preferred embodiment the indazolyl derivative of the invention is an indazolyl derivative of Formula Ia or Ib, wherein A' represents N or $CR^2$, wherein $R^2$ is as defined below; and A" represents N or CH; provided, however, that only one of A' and A" represents N.

In a more preferred embodiment A' represents N; and A" represents CH.

In another more preferred embodiment A' represents $CR^2$, wherein $R^2$ represents hydrogen, alkyl, in particular methyl, ethyl, propyl or isopropyl, or cycloalkyl; and A" represents N.

In a third more preferred embodiment A' represents $CR^2$, wherein $R^2$ represents hydrogen or methyl; and A" represents N.

In a fourth more preferred embodiment A' represents $CR^2$, wherein $R^2$ hydrogen, alkyl, in particular methyl, ethyl, propyl or isopropyl, or cycloalkyl; and A" represents CH.

In a fifth more preferred embodiment A' represents $CR^2$, wherein $R^2$ hydrogen or methyl; and A" represents CH.

In a sixth preferred embodiment the indazolyl derivative of the invention is an indazolyl derivative of Formula Ia or Ib, wherein $R^1$, $R^2$, $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; or $R^1$ and $R^2$ together with the heteroaromatic ring to which they are attached form a benzo-fused ring; and $R^3$ and $R^4$, independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In a more preferred embodiment $R^1$, $R^2$, $R^3$ and $R^4$, independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; or $R^1$ and $R^2$ together with the heteroaromatic ring to which they are attached form a benzo-fused ring; and $R^3$ and $R^4$, independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In an even more preferred embodiment $R^1$, $R^2$, $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In a still more preferred embodiment $R^1$, $R^2$, $R^3$ and $R^4$, independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In another more preferred embodiment $R^1$ and $R^2$, independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; and $R^3$ and $R^4$, independently of each other, represent hydrogen, alkyl-carbonyl-amino, nitro or amino.

In an even more preferred embodiment $R^1$ and $R^2$, independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; and $R^3$ and $R^4$ both represent hydrogen.

In a still more preferred embodiment $R^1$ and $R^2$, independently of each other, represent hydrogen, alkyl, and in particular methyl, cycloalkyl or amino; and $R^3$ and $R^4$, independently of each other, represent hydrogen, alkyl-carbonyl-amino, and in particular methyl-carbonyl-amino, nitro or amino.

In a yet more preferred embodiment one of $R^1$ and $R^2$ represents hydrogen; and the other of $R^1$ and $R^2$ represents alkyl, and in particular methyl, or amino.

In a further more preferred embodiment one of $R^3$ and $R^4$ represents hydrogen; and the other of $R^3$ and $R^4$ represents alkyl-carbonyl-amino, and in particular methyl-carbonyl-amino, nitro or amino.

In a still further more preferred embodiment $R^1$ and $R^2$, independently of each other, represent hydrogen, alkyl, and in particular methyl, or cycloalkyl; and $R^3$ and $R^4$ both represent hydrogen.

In a third more preferred embodiment $R^1$ represents hydrogen or amino; and $R^2$ represents hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; and $R^3$ and $R^4$, independently of each other, represent hydrogen, alkyl-carbonyl-amino, nitro or amino.

In an even more preferred embodiment $R^1$ represents hydrogen or amino; $R^2$ represents hydrogen or alkyl, and in particular methyl; and $R^3$ and $R^4$, independently of each other, represent hydrogen, alkyl-carbonyl-amino, and in particular methyl-carbonyl-amino, nitro or amino.

In a still more preferred embodiment $R^2$ represents hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; and $R^1$, $R^3$ and $R^4$ all represent hydrogen.

In a yet more preferred embodiment $R^1$ represents amino; $R^2$ represents hydrogen, alkyl and in particular methyl; and $R^3$ and $R^4$ both represent hydrogen.

In a further more preferred embodiment $R^2$ represents hydrogen, alkyl, and in particular methyl, or cycloalkyl; and $R^1$, $R^3$ and $R^4$ all represent hydrogen.

In a still further more preferred embodiment $R^2$ represents hydrogen or methyl; and $R^1$, $R^3$ and $R^4$ all represent hydrogen.

In a fourth more preferred embodiment $R^1$ and $R^2$, both represent hydrogen; and $R^3$ and $R^4$, independently of each other, represent hydrogen, alkyl-carbonyl-amino, and in particular methyl-carbonyl-amino, nitro or amino.

In an even more preferred embodiment $R^1$, $R^2$, $R^3$ and $R^4$ all represent hydrogen.

In a fifth more preferred embodiment $R^1$ and $R^2$ together with the heteroaromatic ring to which they are attached form a benzo-fused ring; and $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In an even more preferred embodiment $R^1$ and $R^2$ together with the heteroaromatic ring to which they are attached form a benzo-fused ring; and $R^3$ and $R^4$, independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In a still more preferred embodiment $R^1$ and $R^2$ together with the heteroaromatic ring to which they are attached form a benzo-fused ring; and $R^3$ and $R^4$, independently of each other, represent hydrogen, alkyl, cycloalkyl, alkyl-carbonyl-amino, nitro or amino.

In a yet more preferred embodiment $R^1$ and $R^2$ together with the heteroaromatic ring to which they are attached form a benzo-fused ring; and $R^3$ and $R^4$, independently of each other, represent hydrogen, alkyl or cycloalkyl.

In a further more preferred embodiment $R^1$ and $R^2$ together with the heteroaromatic ring to which they are attached form a benzo-fused ring; and $R^3$ and $R^4$ both represent hydrogen.

In a most preferred embodiment the indazolyl derivative of the invention is
(4-Chloro-phenyl)-(2-indazol-2-yl-6-methyl-pyrimidin-4-yl)-amine;
(4-Chloro-phenyl)-(2-indazol-1-yl-6-methyl-pyrimidin-4-yl)-amine;
Cyclohexyl-(2-indazol-1-yl-quinazolin-4-yl)-amine;
Cyclohexyl-(2-indazol-1-yl-pyrimidin-4-yl)-amine;
Cyclohexyl-(2-indazol-1-yl-6-methyl-pyrimidin-4-yl)-amine;
(4-Chloro-benzyl)-(2-indazol-2-yl-pyrimidin-4-yl)-amine;
(4-Chloro-benzyl)-(2-indazol-1-yl-pyrimidin-4-yl)-amine;
(4-Chloro-phenyl)-[2-(6-nitro-indazol-2-yl)-pyrimidin-4-yl]-amine;
(4-Chloro-phenyl)-[2-(5-nitro-indazol-2-yl)-pyrimidin-4-yl]-amine;
(4-Chloro-phenyl)-(2-indazol-2-yl-6-methyl-pyrimidin-4-yl)-amine;
(4-Chloro-phenyl)-(6-indazol-1-yl-pyridin-2-yl)-amine;
[6-(3-Chloro-indazol-1-yl)-pyridin-2-yl]-(4-chloro-phenyl)-amine;
(4-Chloro-phenyl)-(6-indazol-2-yl-pyrazin-2-yl)-amine;
(4-Chloro-phenyl)-(6-indazol-1-yl-pyrazin-2-yl)-amine;
N-(4-Chloro-phenyl)-2-indazol-2-yl-pyrimidine-4,5-diamine;
2-[4-(4-Chloro-phenylamino)-pyrimidin-2-yl]-2H-indazol-6-ylamine;
N-{2-[4-(4-Chloro-phenylamino)-pyrimidin-2-yl]-2H-indazol-6-yl}-acetamide; or
N-{2-[4-(4-Chloro-phenylamino)-pyrimidin-2-yl]-2H-indazol-5-yl}-acetamide;
or a pharmaceutically acceptable salt thereof.

Any combination of two or more of the embodiments described herein is considered within the scope of the present invention.

Definition of Substituents

In the context of this invention halo represents fluoro, chloro, bromo or iodo. Thus a trihalomethyl group represents e.g. a trifluoromethyl group, a trichloromethyl group, and similar trihalo-substituted methyl groups.

In the context of this invention a haloalkyl group designates an alkyl group as defined herein, which alkyl group is substituted one or more times with halo. Preferred haloalkyl groups of the invention include trihalomethyl, preferably trifluoromethyl.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention a cycloalkyl group designates a cyclic alkyl group, preferably containing of from three to ten carbon atoms ($C_{3-10}$-cycloalkyl), preferably of from three to eight carbon atoms ($C_{3-8}$-cycloalkyl), including cyclopropyl, cyclobutyl, cyclopentyl, cyclohexyl, cycloheptyl and cyclooctyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above.

In the context of this invention a haloalkoxy group designates an alkoxy group as defined herein, which alkoxy group is substituted one or more times with halo. Preferred haloalkoxy groups of the invention include trihalomethoxy, preferably trifluoromethoxy.

In the context of this invention amino-alkyl designates a "NH-alkyl-" group, i.e. a secondary amino group, wherein alkyl is as defined above. Examples of preferred amino-alkyl groups of the invention include aminomethyl and aminoethyl.

In the context of this invention alkyl-amino-alkyl designates an "alkyl-NH-alkyl-" group, wherein alkyl is as defined above. Examples of preferred alkyl-amino-alkyl groups of the invention include methyl-amino-methyl, ethyl-amino-methyl, methyl-amino-ethyl, and ethyl-amino-ethyl.

In the context of this invention an alkyl-carbonyl-amino group designates an "alkyl-CO—NH—" group, wherein alkyl is as defined above. Preferred alkyl-carbonyl-amino groups of the invention include acetamido.

In the context of this invention a hydroxy-alkyl group designates an alkyl group as defined above, which hydroxyalkyl group is substituted with one or more hydroxy groups. Examples of preferred hydroxy-alkyl groups of the invention include 2-hydroxy-ethyl, 3-hydroxy-propyl, 4-hydroxy-butyl, 5-hydroxy-pentyl and 6-hydroxy-hexyl.

In the context of this invention an alkoxy-alkyl group designates an "alkyl-O-alkyl-" group, wherein alkyl is as defined above. Examples of preferred alkoxy-alkyl groups of the invention include methoxy-methyl, methoxy-ethyl, ethoxy-methyl, and ethoxy-ethyl.

Steric Isomers

The indazolyl derivatives of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The indazolyl derivatives of the present invention may also be resolved by the formation of diastereomeric amides by reaction of the indazolyl derivatives of the present invention with an optically active activated carboxylic acid such as that derived from (+) or (−) phenylalanine, (+) or (−) phenylglycine, (+) or (−) camphanic acid or by the formation of diastereomeric carbamates by reaction of the indazolyl derivatives of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Pharmaceutically Acceptable Salts

The indazolyl derivatives of the invention may be provided in any form suitable for the intended administration. Suitable forms include pharmaceutically (i.e. physiologically) acceptable salts, and pre- or prodrug forms of the indazolyl derivatives of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining an indazolyl derivative of the invention and its pharmaceutically acceptable acid addition salt.

Metal salts of an indazolyl derivative of the invention include alkali metal salts, such as the sodium salt of an indazolyl derivative of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The indazolyl derivatives of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The indazolyl derivatives of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

The indazolyl derivatives of the invention have been subjected to in vitro experiments and found particularly useful as potassium channel modulating agents. More particularly the compounds of the invention are capable of selectively modulating SK1, SK2 and/or SK3 channels.

Therefore, in another aspect, the invention relates to the use of an indazolyl derivative of the invention for the manufacture of medicaments, which medicament may be useful for the treatment or alleviation of a disease or a disorder associated with the activity of potassium channels, in particular SK channels, more particularly SK1, SK2 and/or SK3 channels.

In a preferred embodiment, the disease or a disorder associated with the activity of potassium channels is a respiratory disease, epilepsy, convulsions, seizures, absence seizures, vascular spasms, coronary artery spasms, renal disorders, polycystic kidney disease, bladder spasms, urinary incontinence, bladder outflow obstruction, erectile dysfunction, gastrointestinal dysfunction, secretory diarrhoea, ischaemia, cerebral ischaemia, ischaemic heart disease, angina pectoris, coronary heart disease, autism, ataxia, traumatic brain injury, Parkinson's disease, bipolar disorder, psychosis, schizophrenia, anxiety, depression, mania, mood disorders, dementia, memory and attention deficits, Alzheimer's disease, amyotrophic lateral sclerosis (ALS), dysmenorrhea, narcolepsy, Reynaud's disease, intermittent claudication, Sjorgren's syndrome, arrhythmia, hypertension, myotonic muscle dystrophia, spasticity, xerostomi, diabetes type II, hyperinsulinemia, premature labour, baldness, cancer, irritable bowel syndrome, immune suppression, migraine or pain.

In a more preferred embodiment the disease or a disorder associated with the activity of potassium channels is a respiratory disease, urinary incontinence, erectile dysfunction, anxiety, epilepsy, psychosis, schizophrenia, amyotrophic lateral sclerosis (ALS) or pain.

In another preferred embodiment the disease or a disorder associated with the activity of potassium channels is a respiratory disease, in particular asthma, cystic fibrosis, chronic obstructive pulmonary disease (COPD) or rhinorrhea.

In a third preferred embodiment the disease or a disorder associated with the activity of potassium channels is urinary incontinence.

In a fourth preferred embodiment the disease or a disorder associated with the activity of potassium channels is epilepsy, seizures, absence seizures or convulsions.

In a fifth preferred embodiment the disease or a disorder associated with the activity of potassium channels is a respiratory disease, in particular asthma, cystic fibrosis, chronic obstructive pulmonary disease (COPD) or rhinorrhea.

The compounds tested all showed a biological activity in the micromolar and sub-micromolar range, i.e. of from below 1 to above 100 µM. Preferred compounds of the invention show a biological activity determined as described herein in the in the sub-micromolar and micromolar range, i.e. of from below 0.1 to about 10 µM.

Pharmaceutical Compositions

In yet another aspect the invention provides novel pharmaceutical compositions comprising a therapeutically effective amount of the indazolyl derivatives of the invention.

While an indazolyl derivative of the invention for use in therapy may be administered in the form of the raw indazolyl derivative, it is preferred to introduce the active ingredient, optionally in the form of a physiologically acceptable salt, in a pharmaceutical composition together with one or more adjuvants, excipients, carriers and/or diluents.

In a preferred embodiment, the invention provides pharmaceutical compositions comprising the indazolyl derivatives of the invention, or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The indazolyl derivatives of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The indazolyl derivatives of the present invention can be administered in a wide variety of oral and parenteral dosage forms. It will be obvious to those skilled in the art that the following dosage forms may comprise, as the active component, either an indazolyl derivative of the invention or a pharmaceutically acceptable salt of an indazolyl derivative of the invention.

For preparing pharmaceutical compositions from an indazolyl derivative of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The indazolyl derivatives according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like For topical administration to the epidermis the indazolyl derivatives according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the prevention, treatment or alleviation of a disease or a disorder or a condition of a living animal body, including a human, which disease, disorder or condition is responsive to modulation of potassium channels, in particular SK channels, and which method comprises comprising administering to such a living animal body, including a human, in need thereof a therapeutically-effective amount of a compound of the invention.

The preferred indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

Method A (2-Chloro-6-methyl-pyrimidin-4-yl)-(4-chloro-phenyl)-amine (Intermediate Compound)

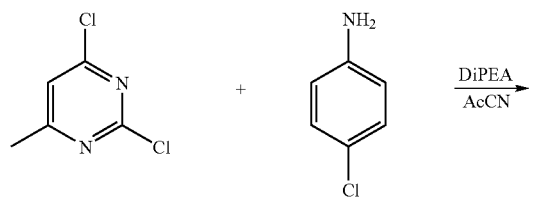

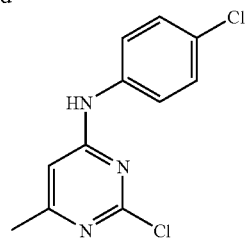

2,4-Dichloro-6-methylpyrimidine (10 g, 61.3 mmol) and 4-chloroaniline (7.83 g, 61.3 mmol) were dissolved in acetonitrile (100 mL). Diisopropylethylamine (21.37 mL, 122.7 mmol) was added and heated to 90° C. for 4 days. The reaction mixture was concentrated in vacuo and the crude product was purified by flash chromatography with ethyl acetate-hexane as eluent to give (2-chloro-6-methyl-pyrimidin-4-yl)-(4-chloro-phenyl)-amine (1.5 g, 10%) as a white solid.

(4-Chloro-phenyl)-(2-indazol-2-yl-6-methyl-pyrimidin-4-yl)-amine (Compound A1); and (4-Chloro-phenyl)-(2-indazol-1-yl-6-methyl-pyrimidin-4-yl)-amine (Compound A2)

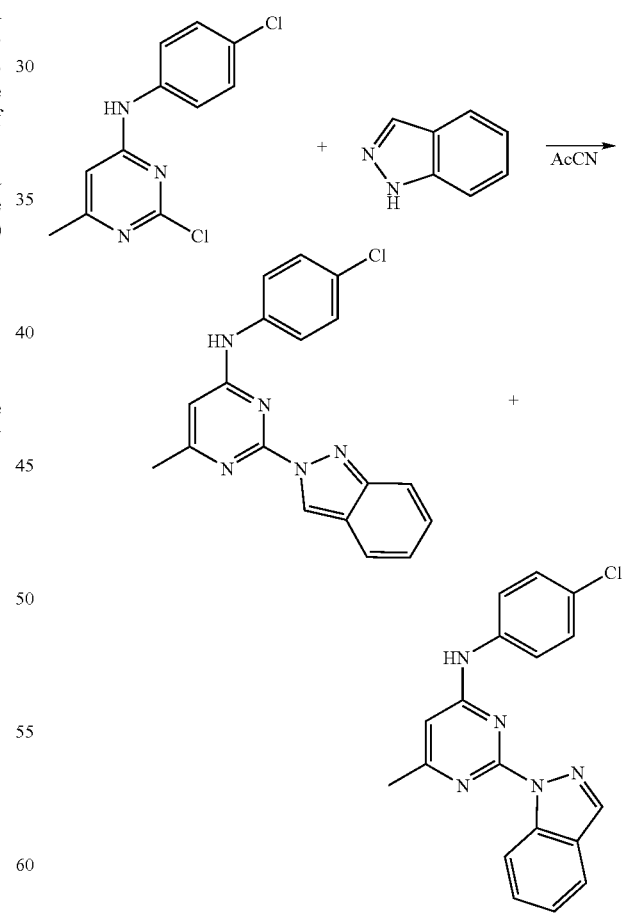

(2-Chloro-6-methyl-pyrimidin-4-yl)-(4-chloro-phenyl)-amine (300 mg, 1.18 mmol) was dissolved in acetonitrile (4 mL), indazole (150 mg, 1.3 mmol) was added and the mixture was heated in a microwave oven at 160° C. for 30 minutes.

The solvent was removed in vacuo and the remaining residue was basified with aqueous sodium hydrogencarbonate and extracted with chloroform. The combined organic phases were dried with sodium sulphate, filtrated and evaporated. The crude product was purified by column chromatography with ethyl acetate-hexane as eluent to give (4-chloro-phenyl)-(2-indazol-2-yl-6-methyl-pyrimidin-4-yl)-amine (56 mg, 14%, mp=224.7-226.7° C.) (LC-ESI-HRMS of [M+H]+ shows 336.1019 Da. Calc. 336.101598 Da, dev. 0.9 ppm) as a white solid and (4-chloro-phenyl)-(2-indazol-1-yl-6-methyl-pyrimidin-4-yl)-amine (21 mg, 5.3%, mp=166.7-168.7° C.) (LC-ESI-HRMS of [M+H]+ shows 336.1007 Da. Calc. 336.101598 Da, dev. −2.7 ppm) as a white solid.

Cyclohexyl-(2-indazol-1-yl-quinazolin-4-yl)-amine (Compound A3)

Was prepared according to Method A from 2,4-dichloro-quinazoline, cyclohexylamine and indazole. Mp=278.1-281.4° C. LC-ESI-HRMS of [M+H]+ shows 344.1879 Da. Calc. 344.18752 Da, dev. 1.1 ppm.

Cyclohexyl-(2-indazol-1-yl-pyrimidin-4-yl)-amine (Compound A4)

Was prepared according to Method A from 2,4-dichloro-pyrimidine, cyclohexylamine and indazole. LC-ESI-HRMS of [M+H]+ shows 294.173 Da. Calc. 294.17187 Da, dev. 3.8 ppm.

Cyclohexyl-(2-indazol-1-yl-6-methyl-pyrimidin-4-yl)-amine (Compound A5)

Was prepared according to Method A from 2,4-dichloro-6-methylpyrimidine, cyclohexylamine and indazole. LC-ESI-HRMS of [M+H]+ shows 308.1859 Da. Calc. 308.18752 Da, dev. −5.3 ppm.

(4-Chloro-benzyl)-(2-indazol-2-yl-pyrimidin-4-yl)-amine (Compound A6); and (4-Chloro-benzyl)-(2-indazol-1-yl-pyrimidin-4-yl)-amine (Compound A7)

Was prepared according to Method A from 2,4-dichloro-pyrimidine, 4-chlorobenzylamine and indazole. Compound A6 LC-ESI-HRMS of [M+H]+ shows 336.1001 Da. Calc. 336.101598 Da, dev. −4.5 ppm. Compound A7 LC-ESI-HRMS of [M+H]+ shows 336.1006 Da. Calc. 336.101598 Da, dev. −3 ppm.

(4-Chloro-phenyl)-[2-(6-nitro-indazol-2-yl)-pyrimidin-4-yl]-amine (Compound A8)

Was prepared according to Method A from 2,4-dichloro-pyrimidine, 4-chloroaniline and 6-nitroindazole. LC-ESI-HRMS of [M+H]+ shows 367.0717 Da. Calc. 367.071027 Da, dev. 1.8 ppm.

(4-Chloro-phenyl)-[2-(5-nitro-indazol-2-yl)-pyrimidin-4-yl]-amine (Compound A9)

Was prepared according to Method A from 2,4-dichloro-pyrimidine, 4-chloroaniline and 5-nitroindazole. LC-ESI-HRMS of [M+H]+ shows 367.0692 Da. Calc. 367.071027 Da, dev. −5 ppm.

(4-Chloro-phenyl)-(2-indazol-2-yl-5-nitro-pyrimidin-4-yl)-amine (Intermediate Compound)

Was prepared according to Method A from 2,4-dichloro-5-nitropyrimidine, 4-chloroanaline and indazole.

Method B

Acetic acid N'-benzyl-hydrazide (Intermediate Compound)

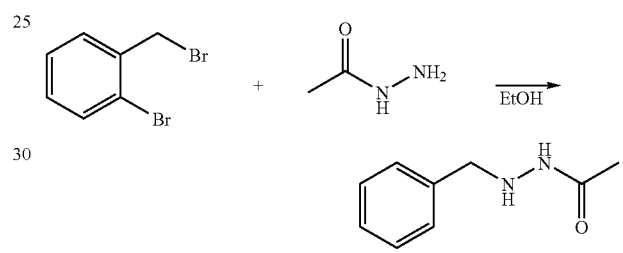

Acetic hydrazide (1.78 g, 24 mmol) was dissolved in ethanol (20 mL) and cooled to 0° C. A solution of 2-bromobenzyl bromide (2 g, 8 mmol) in ethanol (10 mL) was added slowly and stirred at room temperature overnight. The reaction mixture was concentrated under reduced pressure and the crude product was purified by column chromatography with ethyl acetate-hexane as eluent to give acetic acid N'-benzyl-hydrazide (1.7 g, 87%) as a white solid.

Acetic acid N'-(2-bromo-benzyl)-N'-[4-(4-chloro-phenylamino)-6-methyl-pyrimidin-2-yl]-hydrazide (Intermediate Compound)

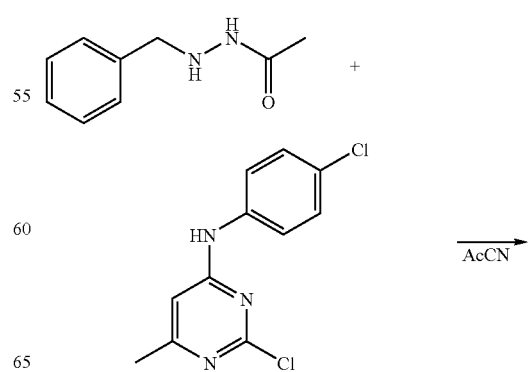

-continued

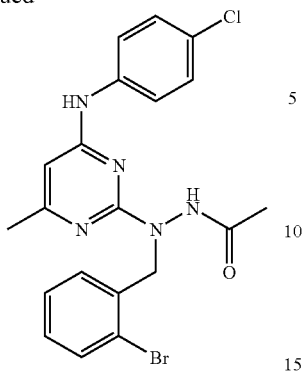

Acetic acid N'-benzyl-hydrazide (1.6 g, 6.58 mmol) and (2-chloro-6-methyl-pyrimidin-4-yl)-(4-chloro-phenyl)-amine (0.84 g, 3.29 mmol) were dissolved in acetonitrile (10 mL) in a sealed wessel. The reaction mixture was heated on a sand bath at 100° C. for 4 days. The resulting solid was filtered off, washed with chloroform and concentrated in vacuo to give acetic acid N'-(2-bromo-benzyl)-N'-[4-(4-chloro-phenylamino)-6-methyl-pyrimidin-2-yl]-hydrazide (0.5 g, 33%) as a white solid.

{2-[N-(2-Bromo-benzyl)-hydrazino]-6-methyl-pyrimidin-4-yl}-(4-chloro-phenyl)-amine (intermediate Compound)

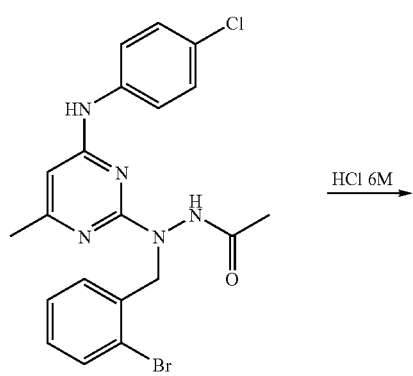

Acetic acid N'-(2-bromo-benzyl)-N'-[4-(4-chloro-phenylamino)-6-methyl-pyrimidin-2-yl]-hydrazide (0.4 g, 0.87 mmol) was suspended in aqueous hydrochloric acid (6 M, 50 mL) and heated to 100° C. for 3 days. The reaction mixture was diluted with water (50 mL), basified with solid sodium hydrogencarbonate and extracted with chloroform (3×50 mL). The combined organic phases were washed with brine, dried over sodium sulphate, filtrated and evaporated to give {2-[N-(2-bromo-benzyl)-hydrazino]-6-methyl-pyrimidin-4-yl}-(4-chloro-phenyl)-amine (0.3 g, 82%) as a brown solid.

(4-Chloro-phenyl)-(2-indazol-2-yl-6-methyl-pyrimidin-4-yl)-amine (Compound B1; Identical to Compound A1 but Obtained by an Alternative Route of Synthesis)

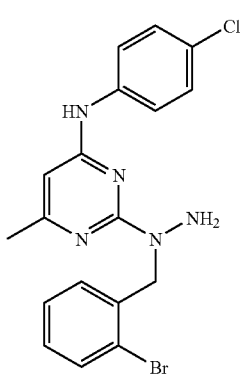

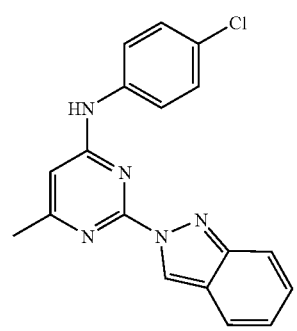

{2-[N-(2-Bromo-benzyl)-hydrazino]-6-methyl-pyrimidin-4-yl}-(4-chloro-phenyl)-amine (0.3, 0.72 mmol), 1,1'-bis(diphenylphosphino)ferrocene (30 mg, 0.054 mmol) and potassium tert-butoxide (127 mg, 1.07 mmol) were suspended in toluene and degassed twice. Palladium (II) acetate (8 mg, 0.035 mmol) was added and the reaction mixture was heated to 90° C. for 48 hours.

The reaction mixture was filtrated through a pad of celite, washed with chloroform and concentrated in vacuo. The crude product was purified by column chromatography with ethyl acetate-hexane as eluent to give (4-chloro-phenyl)-(2-indazol-2-yl-6-methyl-pyrimidin-4-yl)-amine (50 mg, 20%) as a white solid.

Method C

N-(4-Chloro-phenyl)-formamide (Intermediate Compound)

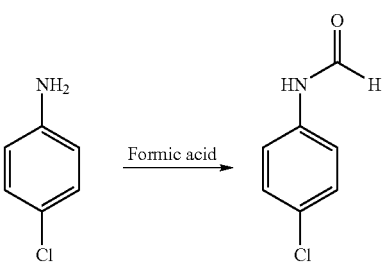

4-Chloroaniline (10 g, 78.4 mmol) and formic acid were heated to reflux for 30 minutes. The reaction mixture was concentrated in vacuo. Water was added and basified with sodium carbonate and extracted with ethyl acetate. The combined organic phases were dried over magnesium sulphate, filtrated and evaporated to give N-(4-chloro-phenyl)-formamide (10.7 g, 88%).

(4-Chloro-phenyl)-(6-fluoro-pyridin-2-yl)-amine (Intermediate Compound)

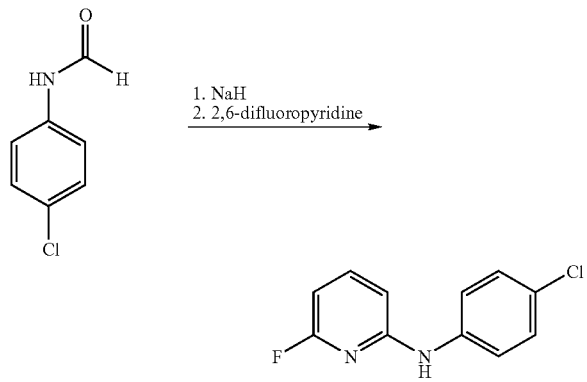

Sodium hydride (1.2 g, 30.9 mmol) was added to a solution of N-(4-chloro-phenyl)-formamide (4 g, 25.7 mmol) in N,N-dimethylformamide (40 mL) and stirred for 15 minutes. 2,6-Difluoropyridine (2.96 g, 25.7 mmol) was added, the reaction mixture was stirred at 70° C. overnight and poured into a stirred ice-water solution. The resulting participate was filtrated off and dried to give (4-chloro-phenyl)-(6-fluoro-pyridin-2-yl)-amine (5.95 g) as the crude product. The crude product was used without further purification.

(4-Chloro-phenyl)-(6-indazol-1-yl-pyridin-2-yl)-amine (Compound C1)

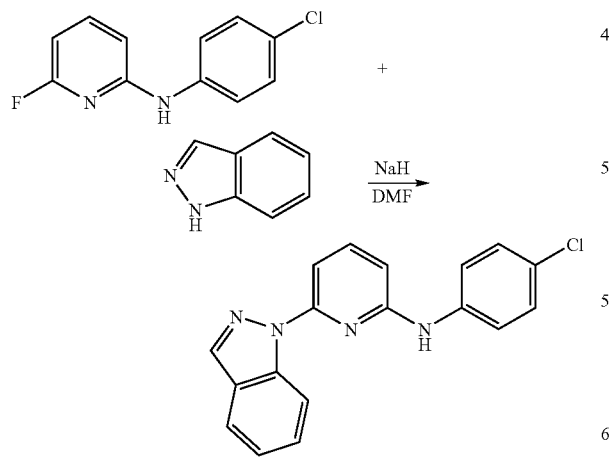

Sodium hydride (325 mg, 8.12 mmol) was added to a solution of indazole (800 mg, 6.77 mmol) in N,N-dimethylformamide (10 mL) and stirred for 30 minutes. (4-Chloro-phenyl)-(6-fluoro-pyridin-2-yl)-amine (1.55 g, 6.77 mmol) was added and the reaction mixture was stirred at 80° C. overnight. The mixture was poured into a stirred ice-water solution and extracted with ethyl acetate. The combined organic phases were dried over magnesium sulphate, filtrated and concentrated in vacuo. The crude product was purified by column chromatography with ethyl acetate-heptane as eluent to give (4-chloro-phenyl)-(6-indazol-1-yl-pyridin-2-yl)-amine (230 mg, 11%) as an yellow solid. LC-ESI-HRMS of [M+H]+ shows 321.0901 Da. Calc. 321.090699 Da, dev. −1.9 ppm

[6-(3-Chloro-indazol-1-yl)-pyridin-2-yl]-(4-chloro-phenyl)-amine (Compound C2)

Was prepared according to Method C from 2,6-difluoropyridine, 3-chloroindazole and 4-chloroaniline. LC-ESI-HRMS of [M+H]+ shows 355.0528 Da. Calc. 355.051727 Da, dev. 3 ppm.

Method D

N-(4-Chloro-phenyl)-N-(6-chloro-pyrazin-2-yl)-2,2-dimethyl-propionamide (Intermediate Compound)

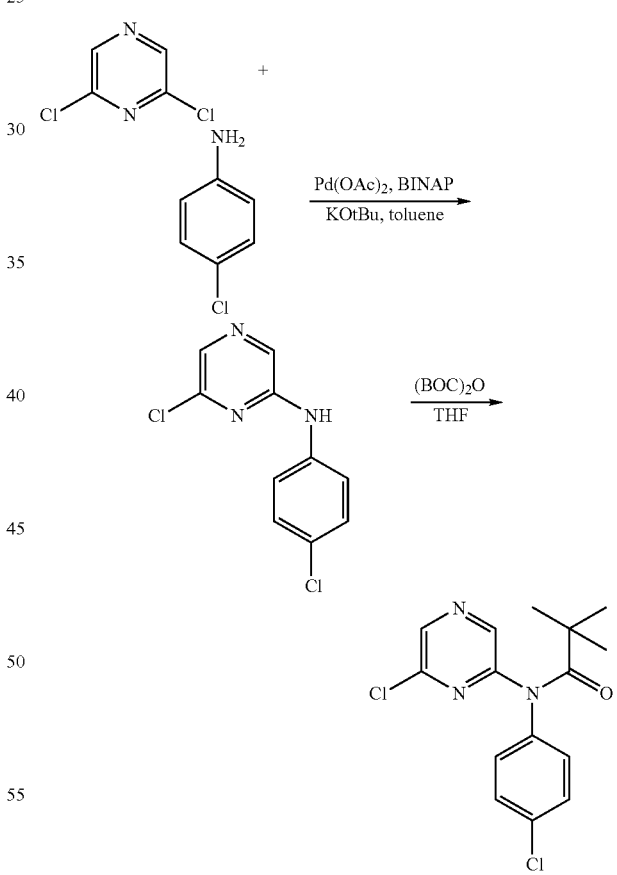

A mixture of 2,6-dichloropyrazine (10 g, 67.12 mmol), 4-chloroaniline (61.02 mmol) and sodium-tert-butoxide (7.78 g, 79.33 mmol) were dissolved in toluene (250 mL) and degassed with argon for 30 min. (±)-2,2'-Bis(diphenylphosphino)-1,1'-binaphtalene ((±)-BINAP) (2.51 g, 4.03 mmol) and palladium (II) acetate (452 mg, 2.01 mmol) were added. The mixture was degassed for further 15 minutes and stirred at 105° C. overnight. The reaction was quenched with water and the phases separated. The aqueous phase was extracted with ethyl acetate and the combined organic phases were dried over sodium sulphate, filtrated and concentrated in vacuo to give 21.48 g the crude product a dark oil. This oil was dissolved in tetrahydrofuran (250 mL), di-tert-butyl dicarbonate (40.36 g, 183.1 mmol) and 4-dimethylaminopyridine (1.5 g, 12.2 mmol) were added and the reaction mixture was heated to reflux for 1 hour. Aqueous saturated ammonium chloride was added and the aqueous phase was extracted with ethyl acetate (4×50 mL). The combined organic phases were dried over sodium sulphate, filtrated and concentrated in vacuo. The crude product was purified by flash chromatography with ethyl acetate-heptane as eluent to give N-(4-chloro-phenyl)-N-(6-chloro-pyrazin-2-yl)-2,2-dimethyl-propionamide (7.2 g, 34%) as an yellow solid.

(4-Chloro-phenyl)-(6-indazol-2-yl-pyrazin-2-yl)-amine (Compound D1); and (4-Chloro-phenyl)-(6-indazol-1-yl-pyrazin-2-yl)-amine (Compound D2)

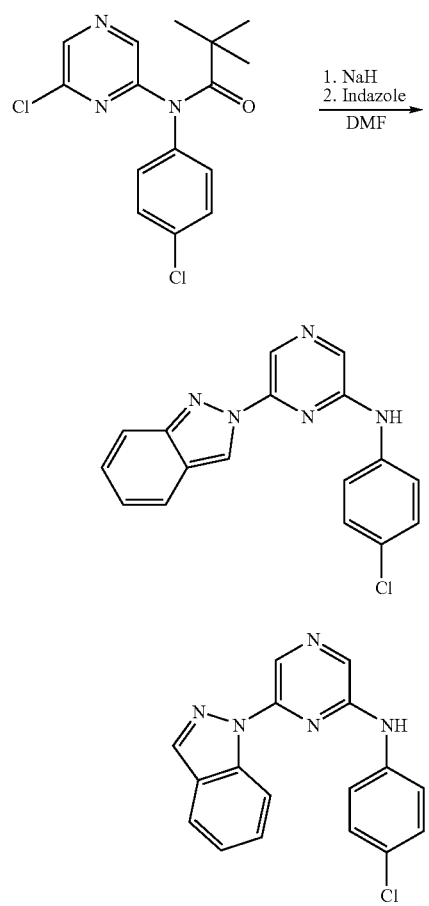

Sodium hydride (180 mg, 4.50 mmol) was added to a suspension of indazole (543 mg, 4.40 mmol) in N,N-dimethylformamide (5 mL) and the reaction mixture was stirred at 50° C. for 20 minutes. To this suspension N-(4-chloro-phenyl)-N-(6-chloro-pyrazin-2-yl)-2,2-dimethyl-propionamide (300 mg, 0.88 mmol) was added and stirred at 100° C. over night. The reaction mixture was quenched with brine and extracted with ethyl acetate (4×15 mL). The combined organic phases were washed with brine, dried over sodium sulphate, filtrated and evaporated. The crude product was purified by column chromatography with ethyl acetate-heptane as eluent to give (4-chloro-phenyl)-(6-indazol-2-yl-pyrazin-2-yl)-amine (17 mg, 13%, Mp 249-252° C., LC-ESI-HRMS of [M+H]+ shows 322.0864 Da. Calc. 322.085948 Da, dev. 1.4 ppm) as a yellow solid, and (4-chloro-phenyl)-(6-indazol-1-yl-pyrazin-2-yl)-amine (19 mg, 12%, Mp. 204-207° C., LC-ESI-HRMS of [M+H]+ shows 322.0876 Da. Calc. 322.085948 Da, dev. 5.1 ppm) as a brown solid.

Method E

N-(4-Chloro-phenyl)-2-indazol-2-yl-pyrimidine-4,5-diamine (Compound E1)

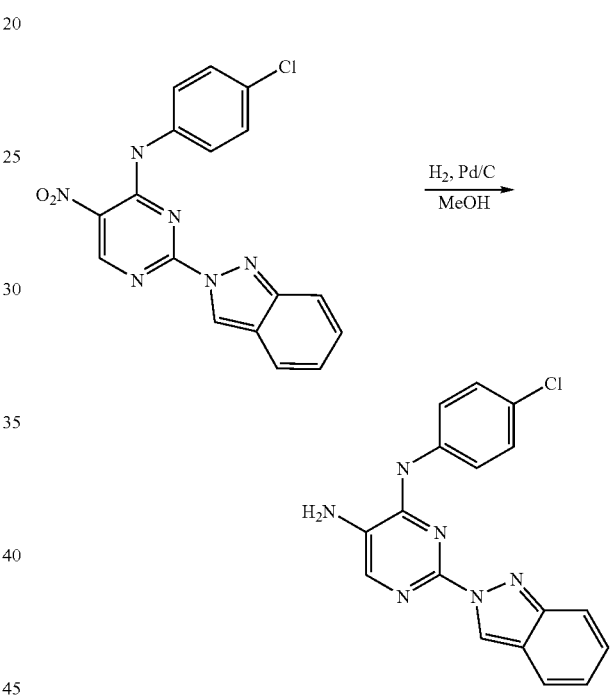

(4-Chloro-phenyl)-(2-indazol-2-yl-5-nitro-pyrimidin-4-yl)-amine (600 mg, 1.64 mmol) was dissolved in methanol (30 mL), palladium an carbon (10%, 150 mg) was added and the reaction mixture was stirred under a hydrogen atmosphere at room temperature over night. Filtration and evaporation gave the crude product which was purified by preparative HPLC to give N-(4-chloro-phenyl)-2-indazol-2-yl-pyrimidine-4,5-diamine (27 mg, 4.9%) as a brown solid. LC-ESI-HRMS of [M+H]+ shows 337.0955 Da. Calc. 337.096847 Da, dev. −4 ppm.

2-[4-(4-Chloro-phenylamino)-pyrimidin-2-yl]-2H-indazol-6-ylamine (Compound E2)

Was prepared according to Method E from (4-chloro-phenyl)-[2-(6-nitro-indazol-2-yl)-pyrimidin-4-yl]-amine. LC-ESI-HRMS of [M+H]+ shows 337.0959 Da. Calc. 337.096847 Da, dev. −2.8 ppm.

Method F

N-{2-[4-(4-Chloro-phenylamino)-pyrimidin-2-yl]-2H-indazol-6-yl}-acetamide (Compound F1)

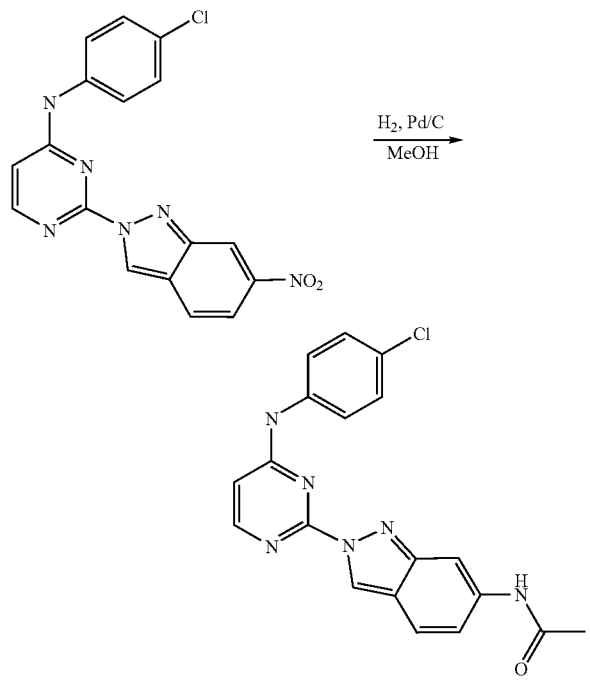

(4-Chloro-phenyl)-[2-(6-nitro-indazol-2-yl)-pyrimidin-4-yl]-amine (500 mg, 1.36 mmol) and iron powder (152 mg, 2.73 mmol) was suspended in acetic anhydride (10 mL) and acetic acid (10 mL). The reaction mixture was heated to 100° C. over night and concentrated in vacuo. Water (30 mL) was added followed by extraction with chloroform (3×30 mL). The combined organic layers were washed with water and brine, dried over anhydrous sodium sulphate, filtrated and concentrated in vacuo to give the crude product as a brown solid. Preparative HPLC gave N-{2-[4-(4-chloro-phenylamino)-pyrimidin-2-yl]-2H-indazol-6-yl}-acetamide (35.2 mg, 6%) as a purple solid. LC-ESI-HRMS of [M+H]+ shows 379.1073 Da. Calc. 379.107412 Da, dev. −0.3 ppm.

N-{2-[4-(4-Chloro-phenylamino)-pyrimidin-2-yl]-2H-indazol-5-yl}-acetamide (Compound F2)

Was prepared according to Method F from (4-chloro-phenyl)-[2-(5-nitro-indazol-2-yl)-pyrimidin-4-yl]-amine. LC-ESI-HRMS of [M+H]+ shows 379.1088 Da. Calc. 379.107412 Da, dev. 3.7 ppm.

Example 2

Biological Activity

This example demonstrates the biological activity of a compound representative of the invention (Compound A1). The ionic current through small-conductance $Ca^{2+}$-activated $K^+$ channels (SK channels, subtype 3) is recorded using the whole-cell configuration of the patch-clamp technique.

HEK293 tissue culture cells expressing hSK3 channels were grown in DMEM (Dulbecco's Modified Eagle Medium) supplemented with 10% FCS (foetal calf serum) at 37° C. in 5% $CO_2$. At 60-80% confluency, cells were harvested by trypsin treatment and seeded on cover slips.

Experiments are carried out a patch-clamp set-up. Cells plated on coverslips are placed in a 15 μl perfusion chamber (flowrate ~1 ml/min) mounted on an inverted microscope placed on a vibration-free table in a grounded Faraday cage. All experiments are performed at room temperature (20-22° C.). An EPC-9 patch-clamp amplifier (HEKA-electronics, Lambrect, Germany) is connected to a Macintosh computer via an ITC16 interface. Data are stored directly on the hard-disk and analysed by IGOR software (Wavemetrics, Lake Oswega, Oreg., USA).

The whole-cell configuration of the patch-clamp technique is applied. In short: The tip of a borosilicate pipette (resistance 2-4 MΩ) is gently placed on the cell membrane using remote control systems. Light suction results in the formation of a giga seal (pipette resistance increases to more than 1 GΩ) and the cell membrane underneath the pipette is then ruptured by more powerful suction. Cell capacitance is electronically compensated and the resistance between the pipette and the cell interior (the series resistance, Rs) is measured and compensated for. Usually the cell capacitance ranges from 5 to 20 pF (depending on cell size) and the series resistance is in the range 3 to 6 MΩ. Rs- as well as capacitance compensation are updated during the experiments (before each stimulus). All experiments with drifting Rs-values are discharged. Leak-subtractions are not performed.

The extracellular (bath) solution contains (in mM): 154 mM KCl, 0.1 $CaCl_2$, 3 $MgCl_2$, 10 HEPES (pH=7.4 with HCl). The test compound was dissolved in DMSO and then diluted 1000 times in the extracellular solution.

The intracellular (pipette) solution contained: 154 mM KCl, 10 mM HEPES, 10 mM EGTA. Concentrations of $CaCl_2$ and $MgCl_2$ needed to obtain the desired free concentrations of $Ca^{2+}$ (0.3-0.4 μM, $Mg^{2+}$ always 1 mM) were calculated by EqCal software (Cambridge, UK) and added.

After establishment of the whole-cell configuration, voltage-ramps (normally −80 to +80 mV) are applied to the cell every 5 seconds from a holding potential of 0 mV. A stable baseline current is obtained within a period of 100-500 seconds, and the compound is then added by changing to an extracellular solution containing the test compound. Active compounds are quantified by calculating the change in baseline current at −75 mV. For activators a $SC_{100}$ value may be estimated. The $SC_{100}$ value is defined as the Stimulating Concentration required for increasing the baseline current by 100%. The $SC_{100}$ value determined for Compound A1 of the invention was 0.08 μM, which is an indication of its strong SK3 activating properties.

The invention claimed is:

1. A compound of Formula Ia or Ib

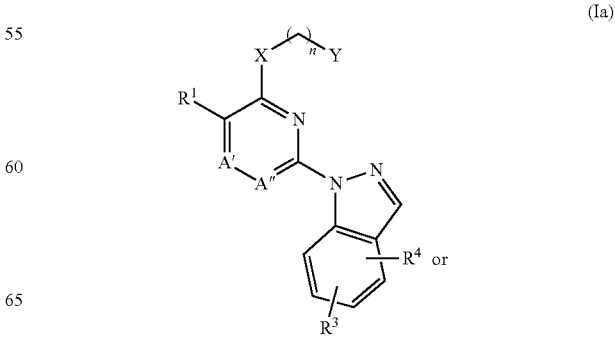

(Ia)

(Ib)

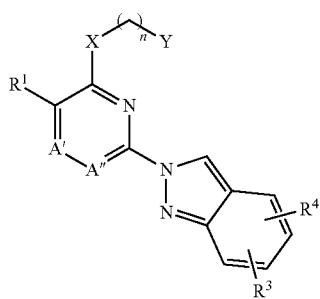

an enantiomer or a mixture of its enantiomers, an N-oxide thereof, or a pharmaceutically acceptable salt thereof, wherein n is 0, 1, 2 or 3;

X represents O, S or NR'; wherein R' represents hydrogen, alkyl, cycloalkyl or cycloalkyl-alkyl;

Y represents alkyl, alkyl-cycloalkyl, cycloalkyl, cycloalkyl-alkyl, amino-alkyl, alkyl-amino, alkyl-amino-alkyl, hydroxy-alkyl, alkoxy-alkyl, alkenyl, or phenyl, which phenyl may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro and amino;

A' represents $CR^2$, wherein $R^2$ is as defined below; and A" represents N; and $R^1$, $R^2$, $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; or $R^1$ and $R^2$ together with the heteroaromatic ring to which they are attached form a benzo-fused ring; and $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

2. The compound of claim 1, being a compound of Formula Ia, an enantiomer or a mixture of its enantiomers, an N-oxide thereof, or a pharmaceutically acceptable salt thereof.

3. The compound of claim 1, an enantiomer or a mixture of its enantiomers, an N-oxide thereof, or a pharmaceutically acceptable salt thereof, wherein n is 0 or 1.

4. The compound of claim 1, an enantiomer or a mixture of its enantiomers, an N-oxide thereof, or a pharmaceutically acceptable salt thereof, wherein X represents NR'; wherein R' represents hydrogen, alkyl, cycloalkyl or cycloalkyl-alkyl.

5. The compound of claim 1, an enantiomer or a mixture of its enantiomers, an N-oxide thereof, or a pharmaceutically acceptable salt thereof, wherein Y represents alkyl, alkyl-cycloalkyl, cycloalkyl, or phenyl, which phenyl may optionally be substituted one or more times with substituents selected from the group consisting of alkyl, cycloalkyl, halo, haloalkyl, haloalkoxy, cyano, nitro and amino.

6. The compound of claim 1, an enantiomer or a mixture of its enantiomers, an N-oxide thereof, or a pharmaceutically acceptable salt thereof, wherein $R^2$ represents hydrogen, alkyl or cycloalkyl.

7. The compound of claim 1, an enantiomer or a mixture of its enantiomers, an N-oxide thereof, or a pharmaceutically acceptable salt thereof, wherein $R^1$, $R^2$, $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

8. The compound of claim 1, which is (4-Chloro-phenyl)-(2-indazol-2-yl-6-methyl-pyrimidin-4-yl)-amine;

(4-Chloro-phenyl)-(2-indazol-1-yl-6-methyl-pyrimidin-4-yl)-amine;

Cyclohexyl-(2-indazol-1-yl-quinazolin-4-yl)-amine;

Cyclohexyl-(2-indazol-1-yl-pyrimidin-4-yl)-amine;

Cyclohexyl-(2-indazol-1-yl-6-methyl-pyrimidin-4-yl)-amine;

(4-Chloro-benzyl)-(2-indazol-2-yl-pyrimidin-4-yl)-amine;

(4-Chloro-benzyl)-(2-indazol-1-yl-pyrimidin-4-yl)-amine;

(4-Chloro-phenyl)-[2-(6-nitro-indazol-2-yl)-pyrimidin-4-yl]-amine;

(4-Chloro-phenyl)-[2-(5-nitro-indazol-2-yl)-pyrimidin-4-yl]-amine;

N-(4-Chloro-phenyl)-2-indazol-2-yl-pyrimidine-4,5-diamine;

2-[4-(4-Chloro-phenylamino)-pyrimidin-2-yl]-2H-indazol-6-ylamine;

N-{2-[4-(4-Chloro-phenylamino)-pyrimidin-2-yl]-2H-indazol-6-yl}-acetamide; or

N-{2-[4-(4-Chloro-phenylamino)-pyrimidin-2-yl]-2H-indazol-5-yl}-acetamide;

an enantiomer or a mixture of its enantiomers, an N-oxide thereof, or a pharmaceutically acceptable salt thereof.

9. A pharmaceutical composition comprising a therapeutically-effective amount of the compound according to claim 1, an enantiomer or a mixture of its enantiomers, an N-oxide thereof, or a pharmaceutically-acceptable addition salt thereof, together with at least one pharmaceutically-acceptable carrier or diluent.

10. The compound of claim 1, being a compound of Formula Ib, an enantiomer or a mixture of its enantiomers, an N-oxide thereof, or a pharmaceutically acceptable salt thereof.

11. The compound of claim 1, an enantiomer or a mixture of its enantiomers, an N-oxide thereof, or a pharmaceutically acceptable salt thereof, wherein $R^1$ and $R^2$ together with the heteroaromatic ring to which they are attached form a benzo-fused ring; and $R^3$ and $R^4$, independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

12. The compound of claim 6, wherein $R^2$ is hydrogen, methyl, ethyl or propyl.

13. A compound of one of the following Formulas:

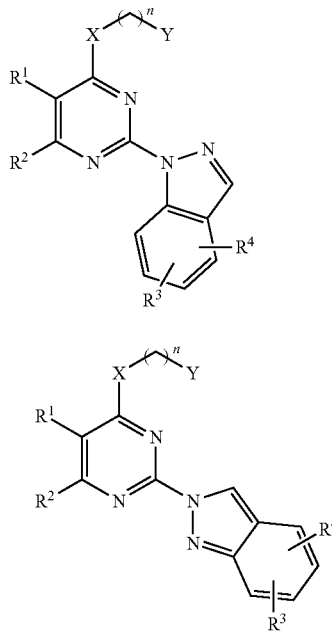

an enantiomer or a mixture of its enantiomers, an N-oxide thereof, or a pharmaceutically acceptable salt thereof, wherein n is 0, 1, 2 or 3;

X represents O, S or NR'; wherein R' represents hydrogen, alkyl, cycloalkyl or cycloalkyl-alkyl;

Y represents alkyl, alkyl-cycloalkyl, cycloalkyl, cycloalkyl-alkyl, amino-alkyl, alkyl-amino, alkyl-amino-alkyl, hydroxy-alkyl, alkoxy-alkyl, alkenyl, or phenyl, which phenyl may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro and amino; and $R^1$, $R^2$, $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino; and $R^3$ and $R^4$, independently of each other, represent hydrogen, alkyl, amino-alkyl, alkyl-amino, alkyl-amino-alkyl, alkyl-carbonyl-amino, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

14. The compound of claim 13, an enantiomer or a mixture of its enantiomers, an N-oxide thereof, or a pharmaceutically acceptable salt thereof wherein X is NH and Y is a phenyl group substituted with a halogen atom.

15. The compound of claim 14, an enantiomer or a mixture of its enantiomers, an N-oxide thereof, or a pharmaceutically acceptable salt thereof wherein Y is a phenyl group substituted with a chlorine atom at the 4-position.

16. The compound of claim 13, an enantiomer or a mixture of its enantiomers, an N-oxide thereof, or a pharmaceutically acceptable salt thereof wherein $R^1$ is hydrogen and $R^2$ is a methyl group.

17. The compound of claim 13, an enantiomer or a mixture of its enantiomers, an N-oxide thereof, or a pharmaceutically acceptable salt thereof wherein $R^3$ and $R^4$ are hydrogen.

18. The compound of any one of claims 13-17, an enantiomer or a mixture of its enantiomers, an N-oxide thereof, or a pharmaceutically acceptable salt thereof which is said compound of the formula (Ib).

19. The compound of claim 13, which is (4-chloro-phenyl)-(2-indazol-2-yl-6-methyl-pyrimidin-4-yl)-amine, an enantiomer or a mixture of its enantiomers, an N-oxide thereof, or a pharmaceutically acceptable salt thereof.

20. A pharmaceutical composition comprising:
a therapeutically effective amount of the compound of claim 13 or 19, an enantiomer or a mixture of its enantiomers, an N-oxide thereof, or a pharmaceutically acceptable salt thereof together; and
at least one pharmaceutically acceptable carrier or diluent.

* * * * *